(12) United States Patent
Kulkarni et al.

(10) Patent No.: US 10,151,677 B2
(45) Date of Patent: Dec. 11, 2018

(54) REAL-TIME OPTICAL FLOW IMAGING TO DETERMINE PARTICLE SIZE DISTRIBUTION

(71) Applicant: Halliburton Energy Services, Inc., Houston, TX (US)

(72) Inventors: Sandeep D. Kulkarni, Kingwood, TX (US); Robert J. Murphy, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 27 days.

(21) Appl. No.: 15/315,041

(22) PCT Filed: Jul. 8, 2014

(86) PCT No.: PCT/US2014/045777
§ 371 (c)(1),
(2) Date: Nov. 30, 2016

(87) PCT Pub. No.: WO2016/007139
PCT Pub. Date: Jan. 14, 2016

(65) Prior Publication Data
US 2017/0191919 A1  Jul. 6, 2017

(51) Int. Cl.
*E21B 47/00* (2012.01)
*E21B 49/00* (2006.01)
(Continued)

(52) U.S. Cl.
CPC ......... *G01N 15/0227* (2013.01); *E21B 21/06* (2013.01); *E21B 21/065* (2013.01);
(Continued)

(58) Field of Classification Search
USPC ......................................................... 382/109
See application file for complete search history.

(56) References Cited

U.S. PATENT DOCUMENTS

| 4,728,190 A | 3/1988 | Knollenberg |
| 6,115,119 A | 9/2000 | Sieracki et al. |

(Continued)

FOREIGN PATENT DOCUMENTS

| JP | 07-333113 | 12/1995 |
| WO | 2010048276 A2 | 4/2010 |
| WO | 2016007139 A1 | 1/2016 |

OTHER PUBLICATIONS

International Search Report and Written Opinion for PCT/US2014/045777 dated Apr. 8, 2015.
(Continued)

*Primary Examiner* — Jerome Grant, II
(74) *Attorney, Agent, or Firm* — Tenley Krueger Tumey L.L.P.

(57) ABSTRACT

An example well system including a drill string extending from a surface location into a wellbore and defining an annulus between the drill string and the wellbore, a fluid circuit extending through the drill string to a bottom of the wellbore and back to the surface location within the annulus, and further extending back to the drill string from the annulus, and one or more flow imaging devices in fluid communication with the fluid circuit to monitor the wellbore fluid and track a real-time particle size distribution (PSD) of one or more particulates suspended within the wellbore fluid.

22 Claims, 4 Drawing Sheets

(51) Int. Cl.
  *G01N 15/02* (2006.01)
  *E21B 21/06* (2006.01)
  *G01N 33/24* (2006.01)
  *E21B 49/02* (2006.01)
  *E21B 49/08* (2006.01)
  *G01N 21/85* (2006.01)
  *G01V 8/10* (2006.01)
  *G01N 21/84* (2006.01)

(52) U.S. Cl.
  CPC .......... *E21B 47/0002* (2013.01); *E21B 49/02* (2013.01); *E21B 49/084* (2013.01); *G01N 21/85* (2013.01); *G01N 33/24* (2013.01); *G01V 8/10* (2013.01); *G01N 2021/8405* (2013.01)

(56) References Cited

U.S. PATENT DOCUMENTS

| | | | |
|---|---|---|---|
| 6,281,489 B1* | 8/2001 | Tubel | E21B 47/00 166/250.15 |
| 7,050,166 B2 | 5/2006 | Bland et al. | |
| 7,796,256 B2 | 9/2010 | Sieracki et al. | |
| 8,345,239 B1 | 1/2013 | Sieracki et al. | |
| 8,427,640 B2 | 4/2013 | Ronaes et al. | |
| 8,812,236 B1 | 8/2014 | Freeman et al. | |
| 2003/0107735 A1 | 6/2003 | Bland et al. | |
| 2007/0159627 A1 | 7/2007 | Johnson | |
| 2008/0307876 A1* | 12/2008 | Lapierre | E21B 21/08 73/152.51 |
| 2010/0128933 A1* | 5/2010 | Derzhi | E21B 49/005 382/109 |
| 2011/0017447 A1* | 1/2011 | Zaleski, Jr. | E21B 43/119 166/250.01 |
| 2011/0153296 A1 | 6/2011 | Sadlier et al. | |
| 2011/0192595 A1 | 8/2011 | Ronaes et al. | |
| 2011/0203845 A1 | 8/2011 | Jamison et al. | |
| 2012/0076349 A1 | 3/2012 | Manri et al. | |
| 2013/0047696 A1* | 2/2013 | Rasmus | G01V 9/00 73/1.67 |
| 2013/0054146 A1* | 2/2013 | Rasmus | E21B 47/06 702/9 |
| 2013/0090855 A1* | 4/2013 | Rasmus | E21B 47/06 702/9 |
| 2013/0107261 A1 | 5/2013 | Duplisea et al. | |
| 2014/0172305 A1* | 6/2014 | Jamison | E21B 47/0905 702/9 |
| 2014/0212983 A1* | 7/2014 | DiFoggio | G01N 33/24 436/119 |
| 2016/0146732 A1* | 5/2016 | Freitag | G01N 15/1434 356/338 |
| 2016/0342916 A1* | 11/2016 | Arceneaux | G06Q 10/06313 |
| 2017/0030181 A1* | 2/2017 | Thomas | E21B 44/04 |
| 2017/0198536 A1* | 7/2017 | Song | E21B 21/00 |
| 2017/0202272 A1* | 7/2017 | Holden | A41C 3/0035 |
| 2018/0050347 A1* | 2/2018 | Tucker | B01D 19/0094 |

OTHER PUBLICATIONS

Canadian Office Action from Canadian Patent Application No. 2950693,, dated Oct. 23, 2017, 4 pages.

* cited by examiner

REAL-TIME OPTICAL FLOW IMAGING TO DETERMINE PARTICLE SIZE DISTRIBUTION

BACKGROUND

The present disclosure relates to the oil and gas industry and, more particularly, to real-time optical flow imaging of wellbore fluids.

During the drilling and completion of a hydrocarbon-producing well, various wellbore fluids are circulated in and/or out of the well. Such wellbore fluids include, but are not limited to, drilling fluids, drill-in fluids, completion fluids, fracturing fluids, and work-over fluids. While drilling a wellbore, for example, a drilling fluid or "mud" is continuously circulated from a surface location down to the bottom of the wellbore being drilled and back to the surface again. Drilling fluids often include a plurality of particles that impart specific properties (e.g., viscosity, mud weight, and the like) and capabilities (e.g., wellbore strengthening) to the drilling fluid.

Prior to being conveyed downhole, the drilling fluid may be treated by adding or removing various components to obtain a predetermined drilling fluid mixture designed for optimal efficiency of the drilling fluid. Weighting agents, for example, are often added to the drilling fluid to produce a drilling fluid with a desired mud weight (i.e., density). Weighting agents are particles having a specific gravity greater than the base fluid of the drilling fluid and, therefore, are able to affect the equivalent circulating density (ECD) of the drilling fluid. During drilling operations, the ECD is often carefully monitored and controlled relative to the fracture gradient of the subterranean formation. Typically, the ECD during drilling is close to the fracture gradient without exceeding it, and when the ECD exceeds the fracture gradient, a fracture may form in the subterranean formation and drilling fluid may be lost into the formation (often referred to as lost circulation).

Due to natural tendencies, the physical characteristics of the drilling fluid mixture introduced downhole may change during circulation and thereby result in a different particle size distribution (PSD) of drilling fluid components. For example, PSD can change due to the addition of fines or cuttings entrained in the drilling fluid during drilling. Moreover, drilling fluid components are subject to particle size attrition resulting from particles breaking down or otherwise being ground to smaller sizes while circulating through the wellbore. As the particle sizes change, the PSD of the drilling fluid is correspondingly altered. In other cases, drilling fluid components of a certain size may be lost through pores defined in the wellbore wall, and thereby also alter the PSD of the drilling fluid. To counteract such losses, lost circulation materials (LCM) are often added to the drilling fluid mixture to form a filter cake on the wellbore wall and otherwise prevent drilling fluid components from escaping into wellbore pores and/or fissures. Adding the LCM, however, alters the PSD of the drilling fluid, and some LCM compositions are removed from the drilling fluid during operation due to intended consumption or using shaker screens or other solids control units.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
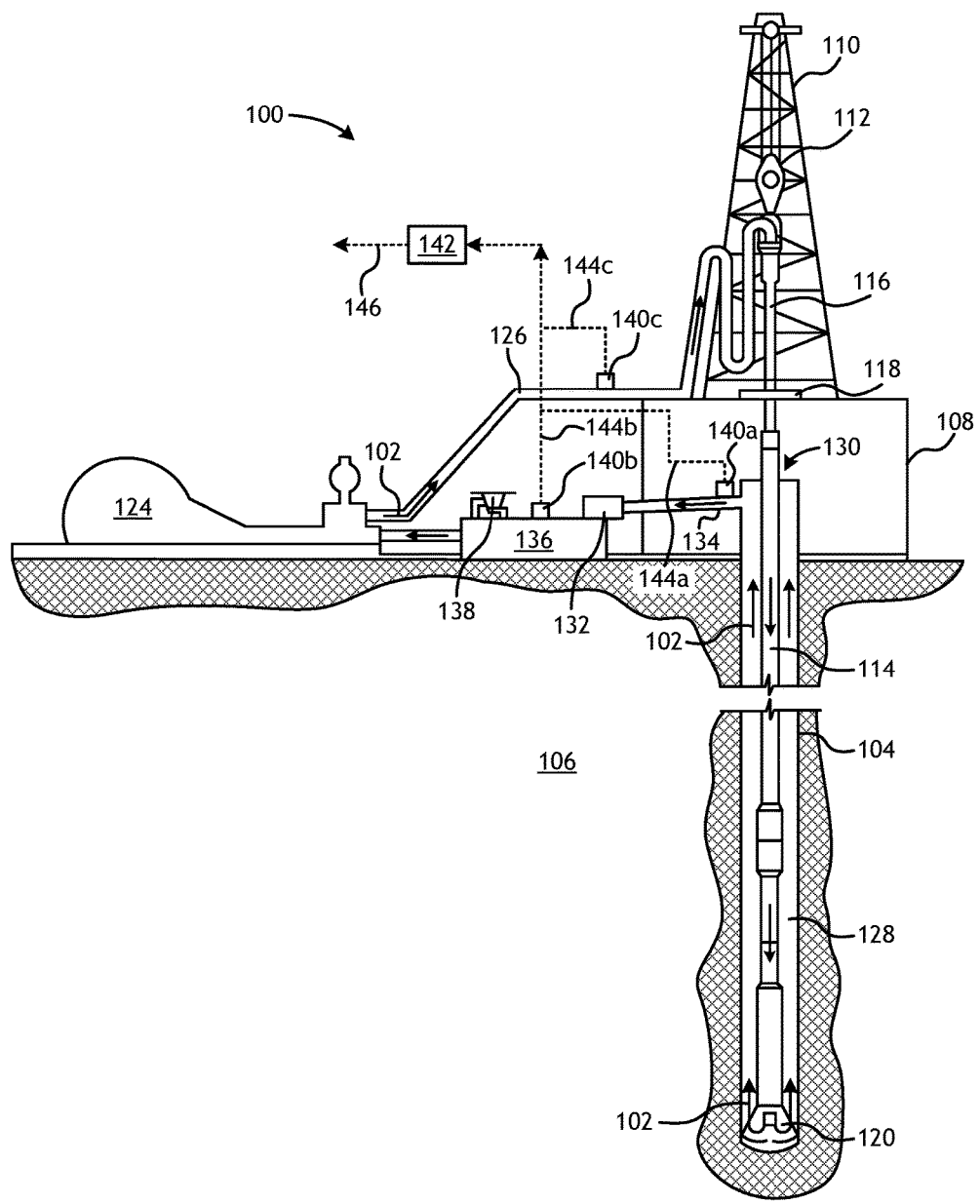
FIG. 1 is a drawing that illustrates an exemplary well system that may employ the principles of the present disclosure to monitor a wellbore fluid, according to one or more embodiments.

The present disclosure relates to the oil and gas industry and, more particularly, to real-time optical flow imaging of wellbore fluids.

There is a growing demand in the industry to find equipment that can supply real-time measurements of PSD for wellbore fluids, and thereby help well operators determine the real-time ECD of the wellbore fluids. Knowing an accurate, real-time PSD of a wellbore fluid can improve control of physical conditions within a subterranean reservoir, such as with the addition of LCM, the identification of fines or cuttings build-up, and help maintain this optimized particle concentration to prevent or mitigate losses. Typically, PSD is measured on a sample of wellbore fluid extracted from a flow line and the sample is then transported to a laboratory where the PSD is determined under laboratory conditions. As can be appreciated, this process can take days and even weeks before the PSD of the wellbore fluid sample is finally obtained.

Some processes and/or equipment for determining PSD may employ laser diffraction methods to determine the PSD of the sample. Laser diffraction-based particle size analysis relies on the fact that particles passing through a laser beam will scatter light at an angle that is directly related to their size. In laser diffraction, PSD may be calculated by comparing the sample's scattering pattern with an appropriate optical model by exploiting the above-described behavior of the particles that pass through the laser beam. More recently, various optical flow systems may transport a fluid within an analytical instrument to an imaging and optical analysis area. In such systems, a liquid sample is typically delivered into the bore of a flow chamber and this sample is interrogated to generate analytical information concerning the nature or properties of the sample.

As used herein, the phrase "optical flow imaging techniques" refers to the process of obtaining an image of particles suspended within a flowing fluid, and then subsequently analyzing the obtained image to determine such things as the number, size, and type of particles depicted in the image. The embodiments described herein provide on-line optical flow imaging techniques that may be used on-site to determine the real-time particle size distribution (PSD) of particulates suspended within various wellbore fluids. Specifically, such techniques may be implemented to track and record the real-time PSD of lost circulation materials (LCM) while the wellbore fluid is circulated in and out of a wellbore. The information obtained may be used to determine the depletion fraction and/or rate of LCM in the wellbore fluid, such as the amount of LCM lost to the subterranean reservoir during circulation. Such information may also correspondingly be used to replenish that fraction of lost LCM to maintain the PSD of LCM in the wellbore fluid at optimal levels. Similarly, the techniques described herein may be used to track and record the real-time PSD of cuttings, weighting materials (e.g., barite), or other solids that may be present in a wellbore fluid circulated through the wellbore, and thereby maintain an optimal PSD of the drilling fluid. The real-time PSD information may prove advantageous in determining the effect of PSD on rheology, sag, and formation damage (if any). In addition, based on imaging of the dispersed phase, different material libraries might be generated to identify the real-time size of an emulsion phase and its concentration in the circulating wellbore fluid.

As used herein, the term "wellbore fluid" refers to a variety of fluids that may be circulated in and/or out of a wellbore of a hydrocarbon-producing well during wellbore drilling and completion operations. Accordingly, "wellbore fluid" may refer to, but is not limited to, drilling fluids, drill-in fluids, completion fluids, fracturing fluids, work-over fluids, pills, spacers, and sweeps. Drilling fluids or drilling "mud" may include water-based drilling fluids, oil-based drilling fluids, synthetic drilling fluids, and the like. Completion fluids or "clean-up" fluids may include, but are not limited to, fresh water, saltwater (e.g., water containing one or more salts dissolved therein), brine (e.g., saturated salt water, chloride salts, bromide salts, combinations thereof, etc.), seawater, a spacer fluid, base fluids, or other treatment fluids known in the art.

As used herein, the terms "particles" and "particulates" include all known shapes of solid materials, including substantially spherical materials, fibrous materials, polygonal materials (such as cubic-shaped materials), and combinations thereof. Use of the terms "particles" and "particulates" does not imply only a single type of particle, but may rather encompass a mixture of various types of particles. Moreover, as used herein, the term "particle size distribution" refers to a list of values or a mathematical function that defines the relative amount by volume of particles or particulates present within a wellbore fluid according to size. In some instances, the particles described herein may have a PSD characterized by $d_{10}$, $d_{25}$, $d_{50}$, $d_{75}$, and $d_{90}$, where the term "$d_n$" (e.g., $d_{10}$, $d_{25}$, $d_{50}$, $d_{75}$, or $d_{90}$) refers to a diameter or size for which n % by volume of the particles have a smaller diameter.

Exemplary particulates that may be monitored to determine PSD in a wellbore fluid according to the present disclosure include, but are not limited to, weighting agents, LCMs, cuttings, neutral density particles, lightweight particles, particles added for stress cage applications, and any combination thereof. Generally, weighting agents may be defined as particulates in a wellbore fluid that have density higher than the base suspending liquid. In other words, the weighting agents typically have a specific gravity greater than the specific gravity of the base fluid. Examples of weighting agents may be particles that comprise barite, hematite, ilmenite, galena, manganese oxide, iron oxide, magnesium tetroxide, magnetite, siderite, celesite, dolomite, manganese carbonate, insoluble polymeric materials, calcium carbonate, marble, polyethylene, polypropylene, graphitic materials, silica, limestone, dolomite, a salt (e.g., salt crystals), shale, bentonite, kaolinite, sepiolite, illite, hectorite, organo-clays, and the like. As will be appreciated, combinations of these types of particles may be used in a weighting agent.

In some embodiments, LCMs may comprise particulates having a low aspect ratio (e.g., less than about 3), fibrous particulates, or both. Suitable LCMs may include, but are not limited to, sand, shale, ground marble, bauxite, ceramic materials, glass materials, metal pellets, high strength synthetic fibers, resilient graphitic carbon, cellulose flakes, wood, resins, polymer materials (cross-linked or otherwise), polytetrafluoroethylene materials, nut shell pieces, cured resinous particulates comprising nut shell pieces, seed shell pieces, cured resinous particulates comprising seed shell pieces, fruit pit pieces, cured resinous particulates comprising fruit pit pieces, composite materials, and any combination thereof. Suitable composite materials may comprise a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and any combination thereof.

Specific examples of suitable LCM particulates may include, but are not be limited to, BARACARB® particulates (ground marble, available from Halliburton Energy Services, Inc.) including BARACARB® 5, BARACARB® 25, BARACARB® 150, BARACARB® 600, BARACARB® 1200; STEELSEAL® particulates (resilient graphitic carbon, available from Halliburton Energy Services, Inc.) including STEELSEAL® 50, STEELSEAL® 150, STEELSEAL® 400 and STEELSEAL® 1000; WALL-NUT® particulates (ground walnut shells, available from Halliburton Energy Services, Inc.) including WALL-NUT® coarse, WALL-NUT® medium, and WALL-NUT® fine; BARAPLUG® (sized salt, available from Halliburton Energy Services, Inc.) including BARAPLUG® 20, BARAPLUG® 50, and BARAPLUG® 3/300; BARAFLAKE® (flake calcium carbonate, available from Halliburton Energy Services, Inc.); and any combination thereof.

Examples of suitable LCM fibers (i.e., fibrous particulates) may include, but are not limited to, fibers of cellulose including viscose cellulosic fibers, oil coated cellulosic fibers, and fibers derived from a plant product like paper fibers; carbon including carbon fibers; melt-processed inorganic fibers including basalt fibers, woolastonite fibers, non-amorphous metallic fibers, metal oxide fibers, mixed metal oxide fibers, ceramic fibers, and glass fibers; polymeric fibers including polypropylene fibers and poly(acrylic nitrile) fibers; metal oxide fibers; mixed metal oxide fibers; protein-based fibrers, soy protein fiber, milk protein fiber and the like; and any combination thereof. Additional examples of suitable LCM fibers may include, but are not limited to, PAN fibers, i.e., carbon fibers derived from poly(acrylonitrile); PANEX® fibers (carbon fibers, available from Zoltek) including PANEX® 32, PANEX® 35-0.125", and PANEX® 35-0.25"; PANOX® (oxidized PAN fibers, available from SGL Group); rayon fibers including BDF™ 456 (rayon fibers, available from Halliburton Energy Services, Inc.); poly(lactide) ("PLA") fibers; alumina fibers; cellulosic fibers; BAROFIBRE® fibers including BAROFIBRE® and BAROFIBRE® C (cellulosic fiber, available from Halliburton Energy Services, Inc.); and any combination thereof.

In some embodiments, LCM particulates and/or fibers may comprise a degradable material. Non-limiting examples of suitable degradable materials that may be used in the present invention include, but are not limited to, degradable polymers (cross-linked or otherwise), dehydrated compounds, and/or mixtures of the two. In choosing the appropriate degradable material, one should consider the degradation products that will result. As for degradable polymers, a polymer is considered to be "degradable" herein if the degradation is due to, inter alia, chemical and/or radical process such as hydrolysis, oxidation, enzymatic degradation, or UV radiation. Polymers may be homopolymers, random, linear, crosslinked, block, graft, and star- and hyper-branched. Such suitable polymers may be prepared by polycondensation reactions, ring-opening polymerizations, free radical polymerizations, anionic polymerizations, carbocationic polymerizations, coordinative ring-opening polymerization, and any other suitable process. Specific examples of suitable polymers include polysaccharides such as dextran or cellulose; chitin; chitosan; proteins; orthoesters; aliphatic polyesters; poly(lactide); poly(glycolide); poly(s-caprolactone); poly(hydroxybutyrate); poly(anhydrides); aliphatic polycarbonates; poly(orthoethers); poly(amino acids); poly(ethylene oxide); polyphosphazenes; and any combination thereof. Of these suitable polymers, aliphatic polyesters and polyanhydrides are preferred.

Dehydrated compounds may be used in accordance with the present invention as a degradable solid particulate. A dehydrated compound is suitable for use in the present invention if it will degrade over time as it is rehydrated. For example, particulate solid anhydrous borate material that degrades over time may be suitable. Specific examples of particulate solid anhydrous borate materials that may be used include, but are not limited to, anhydrous sodium tetraborate (also known as anhydrous borax) and anhydrous boric acid.

Degradable materials may also be combined or blended. One example of a suitable blend of materials is a mixture of poly(lactic acid) and sodium borate where the mixing of an acid and base could result in a neutral solution where this is desirable. Another example would include a blend of poly (lactic acid) and boric oxide, a blend of calcium carbonate and poly(lactic) acid, a blend of magnesium oxide and poly(lactic) acid, and the like. In certain preferred embodiments, the degradable material is calcium carbonate plus poly(lactic) acid. Where a mixture including poly(lactic) acid is used, in certain preferred embodiments the poly(lactic) acid is present in the mixture in a stoichiometric amount, e.g., where a mixture of calcium carbonate and poly(lactic) acid is used, the mixture comprises two poly(lactic) acid units for each calcium carbonate unit. Other blends that undergo an irreversible degradation may also be suitable, if the products of the degradation do not undesirably interfere either with the conductivity of the filter cake or with the production of any of the fluids from the subterranean formation.

Some particles and particulates might be designed to change shape with a predetermined or proper environmental trigger. For example, a fiber may be configured to coil or uncoil depending on a temperature or concentration of one or more components included in a wellbore fluid. The embodiments of the present disclosure may prove advantageous in monitoring the state of such particles.

Neutral density particles are particles or particulates that exhibit a density that is close to that of a base suspending liquid. Example neutral density particles include, but are not limited to, polystyrene particles, polyethylenes, polypropylenes, polybutylenes, polyamides, polystyrenes, polyacronitriles, polyvinyl acetates, styrene-butadienes, polymethylpentenes, ethylene-propylenes, natural rubbers, butyl rubbers, polycarbonates, buckyballs, carbon nanotubes, nanoclays, exfoliated graphites, and any combination thereof. Lightweight particles are particles or particulates that exhibit a density that is less than that of a base suspending liquid. One example lightweight particle is glass bubbles. Particles added for stress cage applications may be similar to the examples provided above for the weighting agents.

Referring to FIG. 1, illustrated is an exemplary well system 100 that may employ the principles of the present disclosure in monitoring a wellbore fluid 102, according to one or more embodiments. As illustrated, the well system 100 may be a drilling facility or rig used to drill a wellbore 104 through various subterranean formations 106. Accordingly, in at least one embodiment, the wellbore fluid 102 may be a type of drilling fluid circulated into the wellbore 104 to enable the drilling operation. In other embodiments, however, the wellbore fluid 102 may be any of the wellbore fluids mentioned herein, without departing from the scope of the disclosure.

In the illustrated embodiment, the well system 100 may include a drilling platform 108 that supports a derrick 110 having a traveling block 112 for raising and lowering a drill string 114. A kelly 116 supports the drill string 114 as it is lowered through a rotary table 118. As will be appreciated by those skilled in the art, a top drive may alternatively be used in place of the kelly 116 and the rotary table 118. A drill bit 120 is attached to the distal end of the drill string 114 and is driven either by a downhole motor and/or via rotation of the drill string 114 from the well surface. As the bit 120 rotates, it creates the wellbore 104 that penetrates the various subterranean formations 106.

A pump 124 (e.g., a mud pump) circulates the wellbore fluid 102 through a feed pipe 126 and to the kelly 116, which conveys the wellbore fluid 102 downhole through an interior conduit defined in the drill string 114 and eventually through one or more orifices in the drill bit 120. The wellbore fluid 102 is then circulated back to the surface via an annulus 128 defined between the drill string 114 and the walls of the wellbore 104 (or casing). During drilling operations, the wellbore fluid 102 (i.e., drilling fluid in this case) serves several purposes, such as providing hydrostatic pressure to prevent formation fluids from entering into the wellbore 104, and keeping the drill bit 120 cool and clean during drilling. The wellbore fluid 102 also serves to carry drill cuttings and solids/particulates (i.e., wellbore fines) out of the wellbore 104 and suspend the drill cuttings and solids/particulates while drilling is paused and/or when the drill bit 120 is moved in and out of the wellbore 104.

As the spent wellbore fluid 102 returns to the surface, it may exit the annulus 128 at a wellhead 130 and may be conveyed to one or more solids control equipment 132 via an interconnecting flow line 134. The solids control equipment 132 may include several fluid rehabilitation devices such as, but not limited to, a shaker (e.g., shale shaker), a centrifuge, a hydrocyclone, a separator, a desilter, a desander, a separator operating with magnetic fields or electric fields, combinations thereof, and the like. The solids control equipment 132 may be configured to substantially remove drill cuttings and other solid particulates from the wellbore fluid 102 and deposit a cleaned wellbore fluid 102 into a nearby retention pit 136 (i.e., a mud pit). The flow path that the wellbore fluid 102 takes to circulate through the wellbore 104 and back to the surface may be characterized and otherwise referred to herein as the "fluid circuit" of the well system 100.

In applications where the wellbore fluid 102 is a drilling fluid, several additives or components may be added to the wellbore fluid 102 to maintain the wellbore fluid 102 in proper working order and otherwise enhance drilling capabilities. In some embodiments, the additives and components may be added to the wellbore fluid 102 via a mixing hopper 138 fluidly coupled to the retention pit 136. The rehabilitated wellbore fluid 102 may then be recirculated and pumped back into the wellbore 104 with the pump 124 via the feed pipe 126.

While circulating through the fluid circuit, the various fluid additives and components suspended within the wellbore fluid 102 may gradually be depleted or otherwise inadvertently removed in the solids control equipment 132. The depletion rate of such additives and components may be counteracted with proper fluid treatment or management of the wellbore fluid 102. Knowing the proper and correct treatment rate in real-time and on-site at the well system 100 may prove useful in optimizing the effectiveness of the wellbore fluid 102.

According to the present disclosure, one or more flow imaging devices 140 (shown as flow imaging devices 140a, 140b, and 140c) may be included at various points throughout the well system 100 to monitor the wellbore fluid 102 and track the real-time PSD of various particulates present within the wellbore fluid 102. As described in greater detail below, each flow imaging device 140a-c may comprise an imaging particle analysis system capable of characterizing particle concentration, size, and shape. The devices 140a-c may further be configured to measure and report the real-time PSD of particulates suspended within the wellbore fluid 102, which may provide an operator with data useful in adjusting various drilling parameters to optimize drilling operations. Exemplary structure and operation of an illustrative flow imaging device similar to the flow imaging devices 140a-c is provided below with respect to FIG. 2.

Each flow imaging device 140a-c may be fluidly arranged in the fluid circuit of the well system 100 such that each is in fluid communication with the wellbore fluid 102 where arranged in the fluid circuit. In some embodiments, for instance, one or more of the flow imaging devices 140a-c may be in direct fluid communication with the wellbore fluid 102 as it circulates through the fluid circuit. In other embodiments, however, one or more of the flow imaging devices 140a-c may fluidly communicate with a conduit or other flow line (not shown) that extends from the fluid circuit to provide an extracted fluid sample of the wellbore fluid 102 to the flow imaging device 140a-c where it is arranged in the fluid circuit.

In some embodiments, as illustrated, a first flow imaging device 140a may be fluidly arranged in the well system 100 to monitor the wellbore fluid 102 as it returns to the surface and otherwise exits out of the wellbore 104 following circulation. More particularly, the first flow imaging device 140a may be fluidly arranged to monitor the wellbore fluid 102 within the flow line 134, the wellhead 130, and/or the annulus 128 near the wellhead 130, and thereby be able to monitor the returning wellbore fluid 102. If an initial PSD of the wellbore fluid 102 were known prior to conveying the wellbore fluid 102 into the wellbore 104, the first flow imaging device 140a may prove useful in providing real-time, on-site data indicative of how the PSD of the wellbore fluid 102 changed after circulating through the wellbore 104.

In some embodiments, a second flow imaging device 140b may be fluidly arranged at or near the retention pit 136, and otherwise following the solids control equipment 132. The second flow imaging device 140b may be configured to monitor the wellbore fluid 102 after it has undergone one or more treatments in the solids control equipment 132, thereby providing a real-time PSD of the wellbore fluid 102 after it has been cleaned. In some embodiments, the second flow imaging device 140b may also be configured to monitor the wellbore fluid 102 in the retention pit 136 as supplementary additive components or particulates are added or otherwise mixed into the wellbore fluid 102 via the mixing hopper 138. For instance, the second flow imaging device 140b may be able to report to an operator when a predetermined PSD of a particular additive component or particulate (e.g., a weighting agent, LCM, etc.) has been added to the wellbore fluid 102 such that the performance of the wellbore fluid 102 is optimized. As will be appreciated, such real-time PSD measurements avoid unnecessarily over-treating the wellbore fluid 102, and thereby saves time and costs.

In some embodiments, a third flow imaging device 140c may be fluidly arranged in the fluid circuit following the retention pit 136, but prior to being reintroduced downhole. For instance, as illustrated, the third flow imaging device 140c may be fluidly arranged at some point along the feed pipe 126 that feeds the wellbore fluid 102 into the drill string 114. In other embodiments, the third flow imaging device 140c may be fluidly arranged between the retention pit 136 and the mud pump 124. The third flow imaging device 140c may be useful in detecting the PSD of the wellbore fluid 102 following the retention pit 136, and thereby confirming whether adequate amounts or concentrations of particulates have been added to the wellbore fluid 102 to ensure optimal or predetermined levels for adequate operation. In other embodiments, the third flow imaging device 140c may be useful in providing an initial PSD reading of the wellbore fluid 102 prior to the wellbore fluid 102 being conveyed into the wellbore 104. Such an initial PSD reading may be compared with the data derived from the first flow imaging device 140a to determine how the PSD of the wellbore fluid 102 changed following circulation through the wellbore 104.

One or all of the flow imaging devices 140a-c may be communicably coupled to a signal processor 142 and configured to convey corresponding output signals 144a-c thereto. The signal processor 142 may be a computer including a processor and a machine-readable storage medium having instructions stored thereon, which, when executed by the processor, cause the signal processor 142 to perform a number of operations, such as determining the PSD of the wellbore fluid 102 at the locations in the fluid circuit where each flow imaging device 140a-c is situated. Moreover, the signal processor 142 may employ one or more algorithms configured to calculate or otherwise determine any differences between any two or more of the output signals 144a-c. Accordingly, in at least one embodiment, the signal processor 142 may be configured to determine how the PSD of the wellbore fluid 102 changes between each monitoring location.

In real-time or near real-time, the signal processor 142 may be configured to provide a resulting output signal 146 corresponding to the PSD of the wellbore fluid 102 at any one of the monitoring locations. In other embodiments, the resulting output signal 146 may provide a measured difference in the PSD between any of the monitoring locations. The resulting output signal 146 may be conveyed, either wired or wirelessly, to a well operator for consideration.

Figure 2:
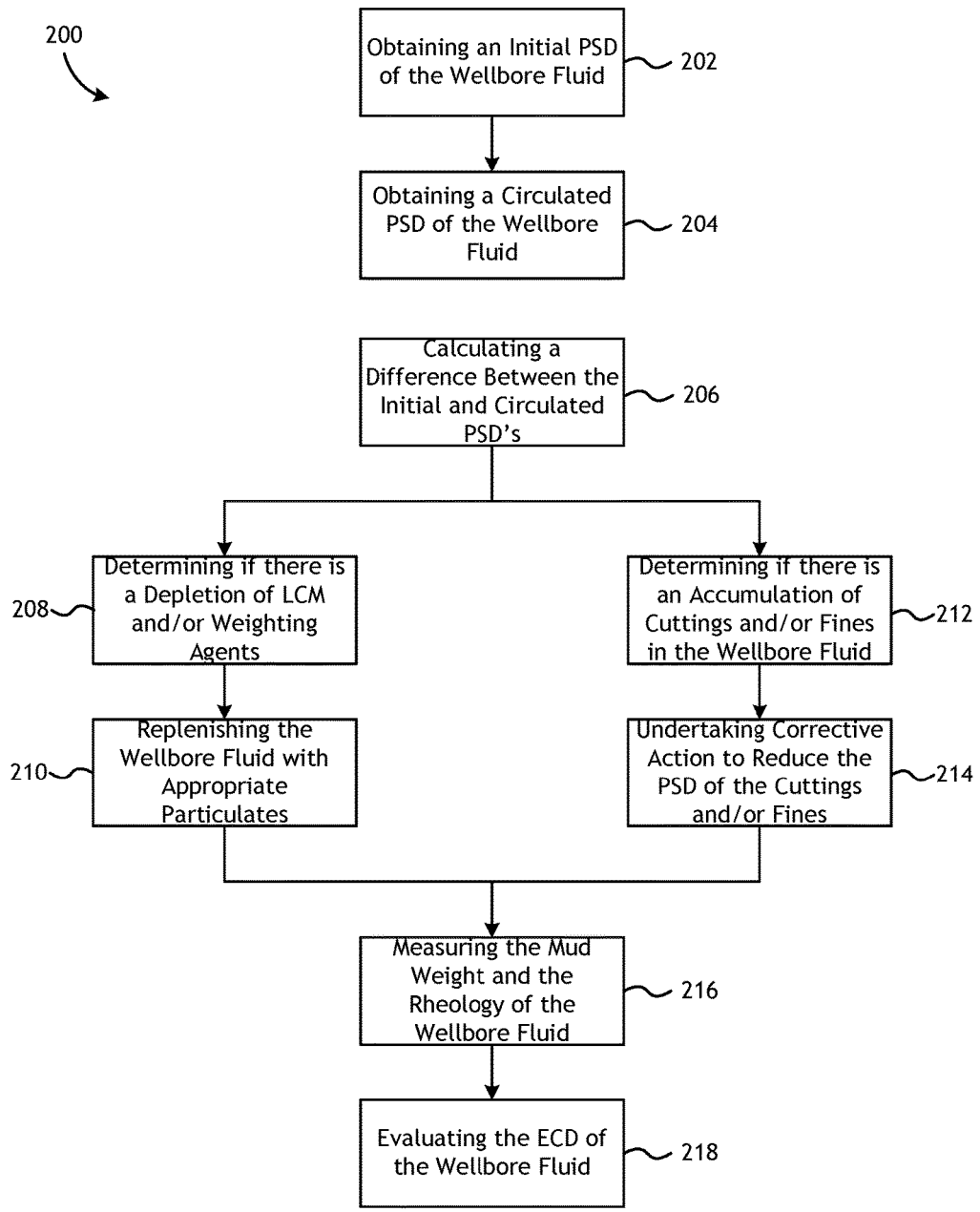
FIG. 2 is a schematic flowchart depicting a method for measuring real-time PSD of a wellbore fluid, according to one or more embodiments

Referring now to FIG. 2, with continued reference to FIG. 1, illustrated is a schematic flowchart of a method 200 for on-site measurement of real-time PSD of a wellbore fluid, according to one or more embodiments. The method 200 may be implemented in the well system 100 of FIG. 1 and, therefore, the wellbore fluid to be monitored may be the wellbore fluid 102 or drilling fluid that is circulated into the wellbore 104. In other embodiments, however, the method 200 may be implemented in a similar well system that circulates a different type of wellbore fluid through a fluid circuit and equally obtains on-site, real-time PSD measurements, without departing from the scope of the disclosure.

According to the method, an initial PSD of the wellbore fluid 102 may be obtained on-site in real-time prior to introducing the wellbore fluid 12 downhole, as at 202. The initial PSD of the wellbore fluid 102 may be obtained by using one or more flow imaging devices 140a-c, such as the third flow imaging device 140c. The particles that may be present or otherwise suspended within the wellbore fluid 102 may include, for example, weighting agents, LCM, fines and/or cuttings, neutral density particles, lightweight particles, particles added for stress cage applications, and any combination thereof. Following circulation of the wellbore fluid 102 in and out of the wellbore 104, a circulated PSD of the wellbore fluid 102 may be obtained on-site and in real-time as the wellbore fluid 102 exits the wellbore 104, as at 204. The circulated PSD of the wellbore fluid 102 may be obtained, for example, by using the first flow imaging device 140a. In at least one embodiment, the circulated PSD of the wellbore fluid 102 may be obtained prior to rehabilitating the wellbore fluid 102 in the solids control equipment 132. In other embodiments, however, the circulated PSD of the wellbore fluid 102 may be obtained after the wellbore fluid has been processed in the solids control equipment 132, without departing from the scope of the disclosure.

The flow imaging devices 140a-c may each convey corresponding output signals 144a-c to the signal processor 142, where each output signal 144a-c is indicative of the PSD of the wellbore fluid 102 at the particular location in the fluid circuit where each flow imaging device 140a-c is situated. The difference between the initial and circulated PSD of the wellbore fluid 102 may then be obtained using the signal processor 142, as at 206. The signal processor 142 may then generate the resulting output signal 146 and convey the same (wired or wirelessly) to a well operator for consideration. In some embodiments, for instance, the resulting output signal 146 may be graphically displayed on a user interface, such as a computer monitor, a hand-held device, or a paper printout. In other embodiments, the resulting output signal 146 may trigger an alarm (audible or visual) configured to alert the operator to an abnormal PSD detection or reading. The resulting output signal 146 may inform an operator as to whether there is a depletion of LCM or weighting agent in the wellbore fluid 102, and/or whether there is an accumulation of fines in the wellbore fluid 102.

If the resulting output signal 146 indicates that a predetermined or preprogrammed range of suitable operation has been surpassed for the wellbore fluid 102, the operator may be notified and thereafter proceed to undertake appropriate corrective action to bring the resulting output signal 146 back to a more reasonable or suitable value. In some embodiments, however, the signal processor 142 may be configured to act autonomously when the resulting output signal 146 is within or without the predetermined or preprogrammed range of suitable operation for the wellbore fluid 10. In such embodiments, the signal processor 142 may autonomously undertake the appropriate corrective action such that the resulting output signal 146 returns to a value within the predetermined or preprogrammed range of suitable operation.

In some embodiments, the resulting output signal 146 may report a depletion of LCM and/or weighting agents in the wellbore fluid 102, as at 208. In such embodiments, one corrective action that may be undertaken to bring the wellbore fluid 102 back into a preprogrammed range of suitable operation may include replenishing the wellbore fluid 102 with appropriate particulates (e.g., weighting agents or LCM), as at 210. This may be done, for instance, using the mixing hopper 138, and may be subsequently verified by once again consulting the resulting output signal 146.

In other embodiments, the resulting output signal 146 may report an accumulation of cuttings and/or fines in the wellbore fluid 102, as at 212. In such embodiments, one or more corrective actions may be undertaken to reduce the PSD of cuttings and/or fines in the wellbore fluid 102 and thereby bring the wellbore fluid 102 back into a preprogrammed range of suitable operation, as at 214. Some corrective actions that may be undertaken to reduce the PSD of cuttings and/or fines in the wellbore fluid 102 include diluting the wellbore fluid 102 with a base oil and/or adding shale/clay stabilizers to the wellbore fluid 102 to avoid further erosion of shales. Another corrective action that may be undertaken upon being alerted to an accumulation of cuttings and fines in the wellbore fluid 102 may include re-processing the wellbore fluid 102 within the solids control equipment 132.

One common problem encountered with some solids control equipment 132 is the inefficient removal of wellbore fines and cuttings. For example, when solids control equipment 132 are not properly tuned, they can sometimes pass unwanted solids or other contaminating particulates into the retention pit 136, thereby having an adverse effect on PSD and degrading the wellbore fluid 102 recirculated back into the wellbore 104. To help avoid this problem, the first and second flow imaging devices 140a,b may be configured to monitor the inlet and outlet of the solids control equipment 132, respectively, and thereby provide an operator with a real-time indication of the efficiency of the solids control equipment 132. In other embodiments, as will be appreciated, only the outlet of the solids control equipment 132 may be monitored and tracked over time to determine how the PSD changes over time. The output signals 144a,b derived from each flow imaging device 140a,b, respectively, may provide the operator with valuable data regarding the PSD of cuttings and/or fines within the wellbore fluid 102 before and after the solids control equipment 132. As such, consulting the first and second output signals 144a,b may serve as a quality control measure for the wellbore fluid 102. When concentrations of cuttings and/or fines are elevated, the operator may decide to re-process the wellbore fluid 102 through the solids control equipment 132 or otherwise alter the parameters thereof in response. As described in more detail below, another option is to add a diluent (e.g., base oil) to bring fine cuttings concentration to within an acceptable range.

In other cases, un-tuned solids control equipment 132 may inadvertently remove valuable additive components or particulates, such as weighting agents or LCM, from the wellbore fluid 102, likewise having an adverse effect on PSD and the performance of the wellbore fluid 102. Accordingly, tuning the solids control equipment 132 may help pass a certain percentage of weighting agents and/or LCM to be recirculated back into the wellbore 104. By comparing the first and second output signals 144a,b (or monitoring only the second output signal 144b over time), an operator may determine whether the solids control equipment 132 is removing the weighting agents and/or LCM from the wellbore fluid 102, or whether the solids control equipment 132 is allowing an appropriate amount to pass into the retention pit 136 along with the cleaned wellbore fluid 102. In order to achieve optimal operation, one or more parameters of the solids control equipment 132 may be adjusted, such as changing out screens or feedrates. This may also prove advantageous in providing an estimate as to how much weighting agents and/or LCM may need to be put back into the wellbore fluid 102 via, for example, the mixing hopper 138.

Once the PSD of the wellbore fluid 102 has been detected, reported, and corrective actions have been undertaken to treat the wellbore fluid 102 and thereby optimize its performance, the mud weight and the rheology of the treated wellbore fluid 102 may be obtained, as at 216. The mud weight and the rheology of the wellbore fluid 102 may be measured with various known tools and devices, such as the Real Time Density and Viscosity (RTDV) Measurement Unit available from Halliburton Energy Services of Houston, Tex. The RTDV is able to measure the density rheology and viscosity of drilling fluids, and may be used on-site at the well system 100 to monitor the wellbore fluid 102. The other fluid properties that can be measured for wellbore fluid 102 may include the oil-to-water ratio, average specific gravity, salt content, etc.

The method 200 may then include evaluating the equivalent circulating density (ECD) of the wellbore fluid 102, as at 218. More particularly, the ECD of a selected LCM and carrier fluid combination may be calculated to ensure that the ECD is in an acceptable operating range. Software may be used to determine the ECD based on the mud weight and rheology of the wellbore fluid 102. (It will be appreciated, however, that ECD may also depend on various operational parameters (e.g., flow rates) and wellbore geometry (e.g., drill string configuration)) More specifically, the ECD at a point in the wellbore annulus 128 is the effective fluid density experienced at that point that comprises of contribution from the intrinsic density of a fluid (i.e., the wellbore fluid 102) and a contribution from flow-induced pressure drop in the annulus 128 above the point in the wellbore 104. The ECD at a given point in the annulus may be determined using the following equation:

$$ECD = (MW) + \frac{\Delta P}{0.052 \times TVD} \quad \text{Equation (1)}$$

where MW is corrected for effect of wellbore temperature, pressure, and fluid compressibility, where ΔP is the total pressure drop in annulus 128 above the given point in the annulus, and where TVD is the vertical depth of the wellbore 104 above the given point in the annulus. The ΔP is evaluated using standard drilling fluids practices (e.g., API RP 13D, rheology and hydraulics of oil-well drilling fluids) or relevant software.

It will be appreciated that the real-time, on-site PSD data obtained using the foregoing method 200 may further prove useful in determining the effect of PSD on rheology, sag, and formation damage. For instance, the PSD information may indicate whether the wellbore fluid 102 is losing larger particles downhole, which may be an indication of loss to the formation (e.g., the formation 106 of FIG. 1). The real-time PSD information may also indicate whether there is sag in the wellbore 104 and the larger particles are accumulating at the bottom of the well or in a dip or elbow area of the wellbore 104. In such cases, the well operator may adjust drilling parameters or alter the mixture of the wellbore fluid 102 so as to mitigate such issues.

Figure 3:
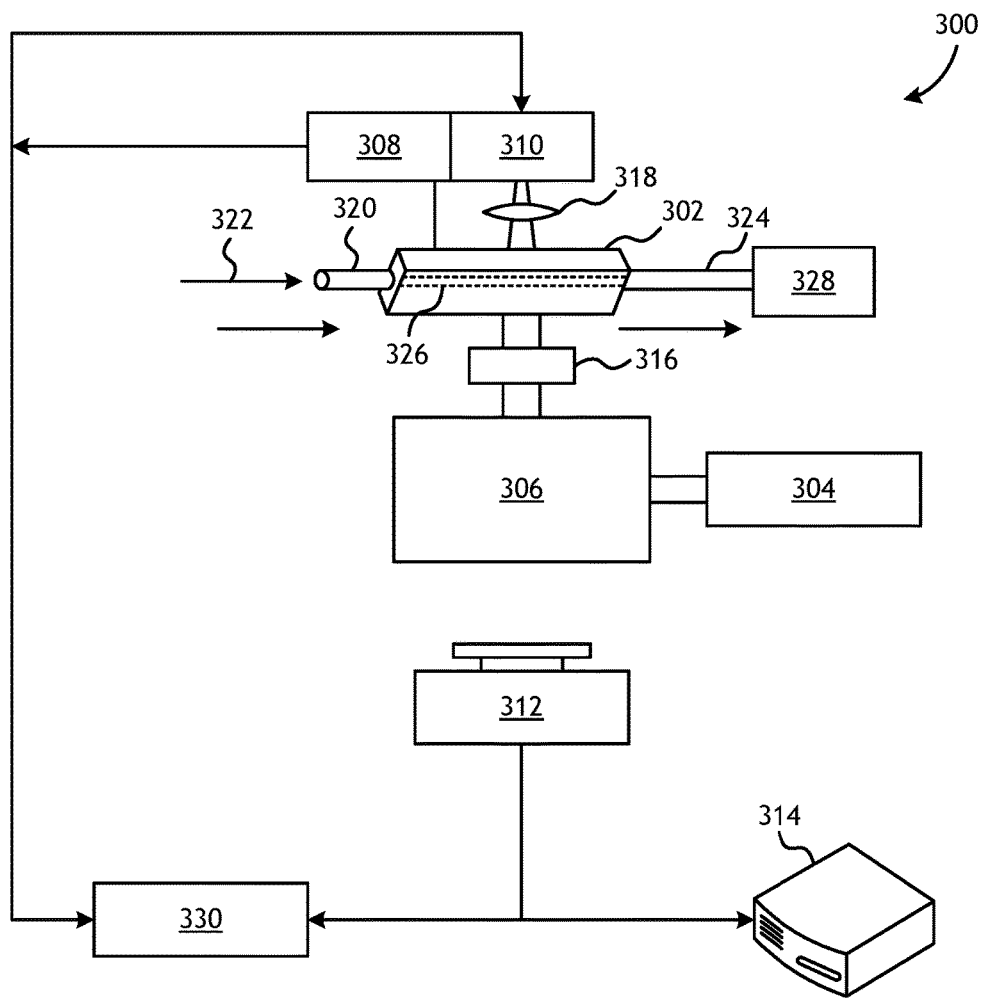
FIG. 3 is a schematic diagram showing an exemplary flow imaging device that may be used in accordance with embodiments of the present disclosure.

Referring now to FIG. 3, with continued reference to FIG. 1, illustrated is a schematic diagram of an exemplary flow imaging device 300 that may be used in accordance with embodiments of the present disclosure. The flow imaging device 300 may be the same as or similar to one or all of the flow imaging devices 140a-c of FIG. 1. Accordingly, the flow imaging device 300 may be an imaging particle analysis system capable of characterizing particle concentration, size, and shape within a fluid, such as the wellbore fluid 102 of FIG. 1.

More particularly, the flow imaging device 300 may comprise an optical flow system used for extracting and monitoring a fluid sample within an imaging and optical analysis area. The fluid sample may be extracted and delivered into a capillary of a flow chamber and interrogated to generate analytical information concerning the nature or properties of the fluid being monitored. In some cases, a laser beam may excite the fluid sample flowing within the capillary and may result in fluorescent energy being emitted and representing the signal information. Any form of such a system capable of performing the foregoing functions may be employed as the flow imaging device 300, provided it generates sufficient resolution to ensure the detection and quantification of particle sizes within the fluid sample. Suitable forms of the flow imaging device 300 include, but are not limited to, the FLOWCAM® and/or FLOWCAM ES® imaging systems provided by Fluid Imaging Technologies, Inc., of Yarmouth, Me. Exemplary embodiments of such imaging systems are described in U.S. Pat. Nos. 6,115,119; 7,796,256; and 8,345,239 and in U.S. Patent Pub. No. 2013/0107261. In at least one embodiment, a flow cytometer may be used as the flow imaging device 300. Other suitable forms of the flow imaging device 300 may include the INFLOW™ particle sizing system available from Canty Process Technology of Dublin, Ireland, or any of the in-line or at-line analyzers also available from Canty Process Technology.

In the illustrated embodiment, the flow imaging device 300 may include a flow chamber 302, a light source 304, optics 306, an image detection system 308, a backlighting generator 310, an image capturing system 312, a computing device 314, a high numerical aperture (NA) objective 316, and a high NA condenser lens 318. The combination of these components of the flow imaging device 300, as arranged and configured as described herein, may enable a user to detect particles in a fluid sample 322 and produce high-resolution images of those particles. As will be appreciated, the fluid sample 322 may be the wellbore fluid 102 of FIG. 1, or an extracted sample thereof at any of the monitoring locations described above. From such high-resolution images, the PSD of the fluid sample 322 may be determined, among other characteristics of the fluid sample 322.

The flow chamber 302 includes an inlet 320 for receiving the fluid sample 322 to be observed and an outlet 324 through which the fluid sample 322 passes after imaging functions have been performed in the flow chamber 302. The flow chamber 302 may be fabricated of a material that does not readily fluoresce, including, but not limited to, microscope glass, rectangular glass extrusions, plastics, semiconductors, crystalline materials, polycrystalline materials, quartz, hot or cold-pressed powders, sapphire, silicon, germanium, zinc selenide, zinc sulfide, or various plastics such as polycarbonate, polymethylmethacrylate (PMMA), polyvinylchloride (PVC), diamond, ceramics, combinations thereof, or the like. The flow chamber 302 may be circular or rectangular in shape, and may define a central channel or capillary 326 through which the fluid sample 322 flows at a predetermined selectable rate. The capillary 326 may be of rectangular configuration and may exhibit a depth of 80 μm, 100 μm, 200 μm, 300 μm, 600 μm, or 1000 μm. The flow chamber 302 is fabricated with a wall thickness that is the same as or similar to the size of a microscope cover slide. The inlet 320 of the flow chamber 302 is communicably coupled to a fluid source for the fluid sample 322, and the outlet 324 is communicably coupled to a pump 328 or another type of downstream means of drawing the fluid sample 322 through the flow chamber 302 and the capillary 326. In other embodiments, a pump (not shown), such as a centrifugal pump, may alternatively be located at the inlet 320 and used to convey the fluid sample 322 through the flow chamber 302 and the capillary 326.

The light source 304 is used to generate fluorescence and scatter excitation light which may be passed through the optics 306 to the flow chamber 302, and thereby resulting in particle fluorescence and/or light scatter. In some embodiments, the light source 304 may be a light emitting diode (LED). In other embodiments, however, the light source 304 may be a laser that uses an excitation filter (not shown). The laser may be, but is not limited to, a 470 nanometer (nm), 488 nm, or 532 nm solid state model laser, and the associated excitation filter may be configured to transmit light at wavelengths longer than the wavelengths of light generated by the laser. Particle fluorescence emissions from the flow chamber 302 may be detected by the detection system 308, which may include one or more emission filters (not shown) and/or one or more high sensitivity photomultiplier tubes (PMT).

The detection system 308 may be configured to detect particles passing through the flow chamber 302 when the light source 304 is activated. Output from the detection system 308 is processed by detection electronics 330 communicably coupled thereto. In some embodiments, the detection electronics 330 may include user-adjusted gain and threshold settings that determine the amount of scatter required for the flow imaging device 300 to acknowledge a passing particle. The detection electronics 330 may be configured to receive input signals and produce output information compatible with the specific needs of the user of the flow imaging device 300. An example of a suitable electronics system capable of performing the signal activation and output information associated with the detection electronics 330 of the flow imaging device 300 is the detection electronics described in U.S. Pat. No. 6,115,119, the contents of which are hereby incorporated by reference to the extent not inconsistent with the present disclosure. Those of ordinary skill in the art will recognize that the specific electronics system described therein may be modified, such as through suitable programming, for example, to trigger desired signal activation and/or to manipulate received signals for desired output information.

If sufficiently lighted particles pass through the flow chamber 302, a signal from the detection system 308 is sent to the detection electronics 330, which, in turn, generates one or more trigger signals that are transmitted to the computing device 314. The computing device 314 may encompass any computing system suitable for receiving information, executing software programs, and producing output information including, but not limited to, images and data that may be observed by a user on a graphical user interface. The computing device 314 may be programmed to store the information received from the detection electronics 330 and to make calculations associated with the particles detected. For example, the computing device 314 may be programmed to provide specific information regarding the shape, dimensions, and/or specific features of the particles. Moreover, the computing device 314 may further be programmed to determine the PSD of the fluid sample 322. In some embodiments, the computing device 314 may be the same as or similar to the signal processor 142 of FIG. 1. In other embodiments, however, the computing device 314 may be communicably coupled to the signal processor 142 such that any output signals (e.g., output signals 144a-c of FIG. 1) generated by the computing device 314 may be conveyed to the signal processor 142 for processing.

The detection electronics 330 may also be coupled, directly or indirectly through the computing device 314 to the backlighting generator 310. The detection electronics 330 and/or the computing device 314 may include an arrangement whereby a user of the flow imaging device 300 may alternatively select a setting to automatically generate a trigger signal at a selectable time interval. The trigger signal may activate the operation of the backlighting generator 310 so that a light flash is generated and directed toward the flow chamber 302. Specifically, the backlighting generator 310 may be a LED or other suitable light generating means that produces a light of sufficient intensity to backlight the flow chamber 302 and image the passing particles suspended within the fluid sample 322. The very high intensity LED flash may be a "white" LED flash, or a flash of another other suitable wavelength, which is flashed on one side of the flow chamber 302 for about 200 μsec (or less).

At the same time, the image capturing system 312 positioned on the opposing side of the flow chamber 302 may be activated to capture an instantaneous image of the particles in the fluid sample 322 when the high intensity flash occurs. The image capturing system 312 may be configured to either retain the captured image, transfer it to the computing device 314, or a combination of the two. The image capturing system 312 may include various characteristics similar to that of a digital camera or an analog camera with a frame-grabber or other means for retaining images. For example, the image capturing system 312 may be, but is not limited to, a CCD firewire camera, a CCD USB-based camera, or any other suitable device that may be used to capture images. The image capturing system 312 may further include computing means, or may be coupled to computing means, for the purpose of retaining images and manipulating those images as desired. Upon receiving the images captured by the image capturing system 312, the computing device 314 may be programmed to measure the size and shape of the particles and/or store the data for later analysis.

As forming part of the optics 306, the flow imaging device 300 also includes the high NA objective 316 and the high NA condenser lens 318. The high NA condenser lens 318 aids in clear illumination of the fluid sample 322 that is to be imaged as flowing within the capillary 326 by focusing the high intensity flash from the backlighting generator 310 to that section. The high NA condenser lens 318 includes characteristics of a numerical aperture of about 1.25 and the high NA objective 316 includes characteristics of a numerical aperture greater than 0.7. The high NA objective 316 may be arranged to focus the illuminated image to the image capturing system 312, and may also be used to focus fluorescence excitation light from the light source 304 onto the flow chamber 302. The high NA objective 316 is selected to have a range of focus or "working distance" which ensures that focus is substantially maintained through the entirety of the cross section of the capillary 326.

Exemplary operation of the flow imaging device 300 is now provided. One or more computer programs may be stored in memory associated with the computing device 314 and, when executed by one or more processors of the computing device 314, may assist in the storing and analyzing of images captured by the image capturing system 312. The light source 304 and imaging optics 306 may first be activated to generate and direct scatter excitation light toward the flow chamber 302 and the fluid sample 322 flowing therein. In some embodiments, the fluid sample 322 may be treated prior to being transferred to the flow chamber 302 for detection. For example, in some embodiments, a user, or the flow imaging device 300 itself, may dilute the fluid sample 322 so as to obtain a fluid that is transparent enough to have any particulates suspended therein captured optically. In other cases, or in addition thereto, the fluid sample 322 may be pre-treated by running it through a shaker or centrifuge (e.g., the solids control unit 132 of FIG. 1) to remove particles of a certain size.

The light source 304 may be activated to generate fluorescence and scatter excitation light, which may pass through the optics 306 and the flow chamber 302 to generate particle fluorescence and/or light scatter of particles suspended within the fluid sample 322. The detection system 308 detects the fluorescing particles passing through the flow chamber 302 and alerts the detection electronics 330, which generates a trigger signal that is transmitted to the computing device 314. Upon receiving the trigger signal, the computing device 314 may operate the image capturing system 312 in conjunction with the backlighting generator 310, which generates a light flash that backlights the capillary 326 so that the image capturing system 312 may instantaneously image the passing particles suspended within the fluid sample 322. The imaging data obtained by the image capturing system 312 may be either stored or transferred to the computing device 314 for processing. In some embodiments, the computing device 314 may be programmed to analyze the imaging data and determine a real-time PSD of the fluid sample 322.

It is to be understood that the computing device 314 (and/or the signal processor 142 of FIG. 1) used to gather the captured image information, perform calculations, and observe features of the captured image information may be associated with local or remote computing means, such as one or more central computers, in a local area network, a metropolitan area network, a wide area network, or through intranet and internet connections. The computing device 314 may include one or more discrete computer processor devices, and the computing device 314 may include computer devices operated by a centralized administrative entity or by a plurality of users located at one or more locations. Moreover, the computing device 314 may be programmed to execute one or more of the functions of the flow imaging device 300.

The computing device 314 may also include one or more library databases that store information related to the use of the flow imaging device 300. For example, such library databases may include known images of example particles of interest such that captured images may be compared to known or similar images of particles of interest and reported to determine PSD of the fluid sample 322. Moreover, the library databases may be populated and updated with information provided by the user in order to optimize operation of the flow imaging device. For instance, the library databases may be populated with image information relating to fluid components that are not of interest (or that need to be accounted for separately) including, but not limited to, air bubbles, water, oil droplets, and other fluid components that may typically be spherical as suspended within the fluid sample 322. Using an algorithm executed by the computing device 314, these fluid components may be compared against other particles suspended within the fluid sample 322, which are not typically spherical. As a result, the algorithm may be configured to omit, not count, or otherwise account separately the substantially spherical fluid components in determining PSD, and thereby obtain a more accurate PSD that does not count unwanted fluid components, such as air bubbles, water, oil droplets, etc.

As will be appreciated, the library databases may alternatively, or in addition thereto, be populated with image information relating to other fluid components that are not of interest (or that need to be accounted for separately), such as fibers and solid particles that may be suspended within the fluid sample 322. Using another algorithm executed by the computing device 314, these fluid components may be compared against other particles suspended within the fluid sample 322 based on several factors including, but not limited to, their respective aspect ratios, material type, color, light intensity information, etc. As a result, the algorithm may be configured to omit, or otherwise not count, or otherwise account separately the fibers and solid particles in determining PSD, and thereby obtain a more accurate PSD.

The foregoing operation of the flow imaging device 300 may be carried out as electronic functions performed through the computing device 314 based on computer programming steps. The functions configured to perform the steps described herein may be implemented in hardware and/or software. For example, particular software, firmware, or microcode functions executing on the computing device 314 can provide the trigger, image capturing, and image analysis functions. Alternatively, or in addition, hardware modules, such as programmable arrays, can be used in the devices to provide some or all of those functions, provided they are programmed to perform the steps described.

Comparative Experimentation

The above-described flow imaging of sample fluids was tested against conventional laser diffraction methods to determine whether PSD data could accurately be obtained using the flow imaging techniques described herein. In no way should the following tests be read to limit, or to define, the scope of the disclosure.

The sample fluid that was monitored in the following tests to measure PSD was a simulated drilling fluid sample comprising mineral oil with weighting agents suspended therein. More particularly, the mineral oil used was XP-07™ synthetic paraffin base fluid with barite particles suspended therein; the volume % of barite in the fluid was approximately 40%. The flow imaging device used to monitor the fluid sample and calculate the PSD of the fluid sample was the FLOWCAM ES® imaging system available through Fluid Imaging Technologies, Inc. The FLOWCAM ES® imaging system is able to take images at frame rates as high as 30 frames/sec, and the lower limit of the particle size measurement is approximately 1 µm while the upper limit is equivalent to the depth of the capillary (i.e., the capillary 326 of FIG. 3).

Prior to being introduced into the flow imaging device, the sample fluid was pre-treated. More particularly, a 0.1 ml portion of the sample fluid was diluted with 5 ml of base oil (XP-07), and then the 0.1 ml portion of the diluted solution was further mixed with 5 ml base oil to obtain a resultant dilution ratio of 2500:1. The other way of dilution was to add 0.1 ml of the drilling fluid directly to 250 ml of diluent. The flow-rate of the sample fluid into the flow chamber of the flow imaging device was maintained at about 1.5 ml/min, and the time required for imaging of the fluid sample was about 1 minute, where approximately 50,000 particles were imaged.

Figure 4:
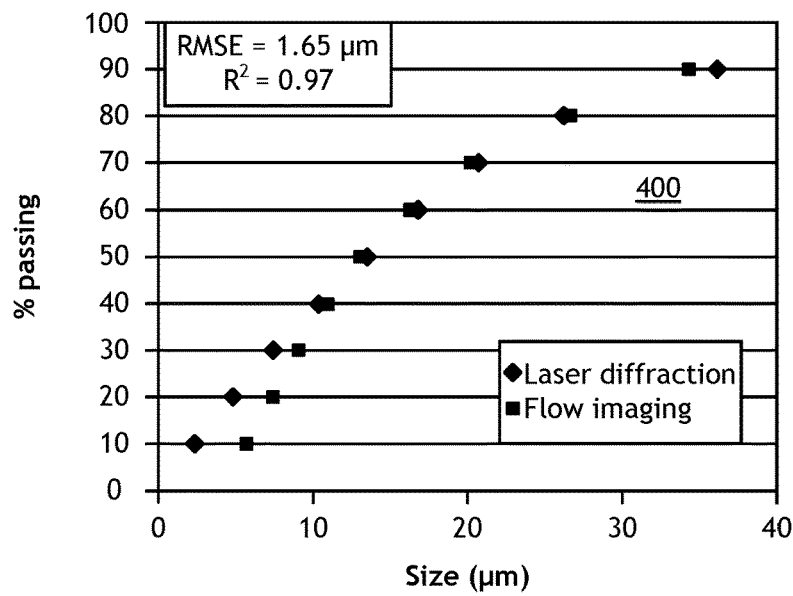
FIG. 4 is a plot that depicts particle-size measurements corresponding to flow imaging in comparison to particle-size measurements performed using standard laser diffraction methods.

TEST 1: With reference to the plot 400 of FIG. 4, particle-size measurements corresponding to flow imaging are depicted in comparison to particle-size measurements performed using a standard laser diffraction method from an analytical lab for the same sample of particles. The diluted fluid sample was run through the flow imaging device six times, and the average of each of the six runs generated nine data points with a standard deviation of ±1 µm. As illustrated in the plot 400, 10% of the particles passing through the flow imaging device were reported as exhibiting a size of less than about 5 microns, whereas 50% of the particles passing through the flow imaging device were reported as exhibiting a size of less than about 12 microns. Moreover, 90% of the particles passing through the flow imaging device were reported as exhibiting a size of less than about 33 microns.

The plot 400 indicates that the measurements based on the flow-imaging method are in excellent agreement with those obtained using standard laser diffraction methods (RMSE=1.65 µm and $R_2$=0.97). Table 1 below shows the $d_{10}$, $d_{50}$, and $d_{90}$ of the fluid sample obtained using the flow-imaging method as compared with that obtained using the laser diffraction method from the analytical lab. As noted in Table 1, the $d_{50}$ and $d_{90}$ from these two methods are in excellent agreement. The variation in $d_{10}$ is likely attributed to the limitation on resolution of the lens and/or filters used in the flow-imaging equipment, which could be improved if required. For instance, the user may improve the $d_{10}$ reading by using better optics, such as more precise lenses with higher magnification. However, this may risk missing the larger sizes of particles.

TABLE 1

| Standard Barite | LASER DIFFRACTION TECHNIQUE (ANALYTICAL LAB) (average of six runs) | FLOW IMAGING TECHNIQUE (Flow-CAM ES ™) (average of six runs) |
| --- | --- | --- |
| $d_{10}$ (µm) | 2.3 | 5.7 |
| $d_{50}$ (µm) | 13.8 | 12.9 |
| $d_{90}$ (µm) | 37.6 | 34.1 |

Figure 5:
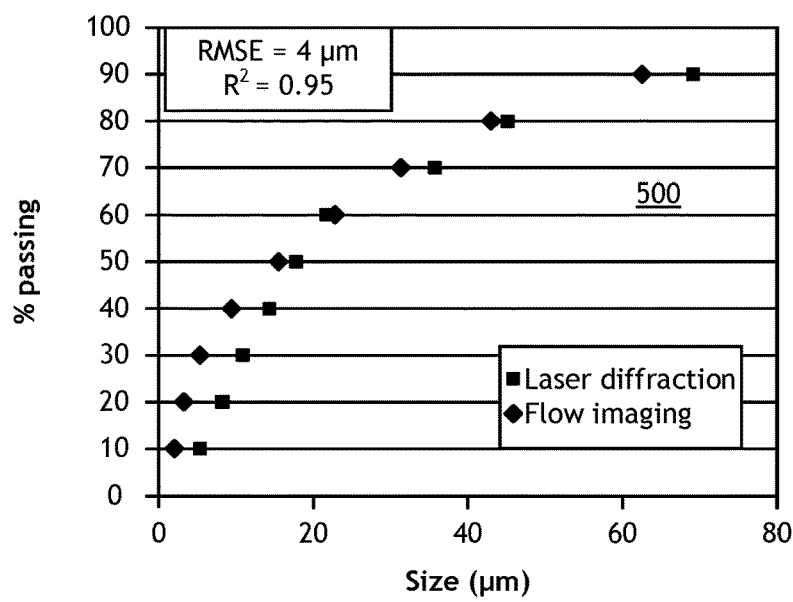
FIG. 5 is another plot that depicts particle-size measurements corresponding to flow imaging in comparison to particle-size measurements performed using standard laser diffraction methods.

TEST 2: With reference to the plot 500 of FIG. 5, the fluid sample tested included additional drilling fluid components, including particles and emulsion. More particularly, the fluid sample included particles consisting of barite, calcium carbonate, fine cuttings, etc., and emulsion. The fluid sample from Test 1 consisted of only barite in base oil (XP-07) while the fluid sample in Test 2 contained many more components suspended in the base oil (XP-07). As a result, the fluid sample in Test 2 is more representative of a drilling fluid while the fluid sample of Test 1 was chosen for simplicity so as to easily verify the consistency of the methods. The resulting mud weight of the fluid sample in Test 2 was 16.7 ppg and the oil-to-water ratio was measured at 83:17. As with Test 1, Test 2 was undertaken to study the accuracy of particle-size measurements based on the flow imaging technique in comparison again with particle-size measurements performed using a standard laser diffraction method from an analytical lab for the same sample of particles.

Moreover, as with Test 1, the fluid sample was diluted and then the diluted fluid sample in Test 2 was run through the flow imaging device six times, and the average of each of the six runs generated nine data points with a standard deviation of ±1 µm. Note that the diluted fluid may or may not have the emulsion in the same form as that of un-diluted. As shown in the plot 500, 10% of the particles passing through the flow imaging device were reported as exhibiting a size of less than about 5 microns, whereas 50% of the particles passing through the flow imaging device were reported as exhibiting a size of less than about 18 microns. Moreover, 90% of the particles passing through the flow imaging device were reported as exhibiting a size of less than about 69 microns.

The plot 500 indicates that the measurements based on the flow-imaging method are again in reasonable agreement with measurements obtained using standard laser diffraction methods (RMSE=4 µm and $R_2$=0.95). The error between the two measurement methods for the fluid sample in Test 2 was slightly larger compared to that for the fluid sample in Test 1. The error might be minimized by developing material libraries configured to remove irrelevant particles, such as water or oil droplets, or air bubbles, for different types of particles and emulsions and adjusting the dilution ratios in the flow-imaging experiments.

Table 2 below denotes the $d_{10}$, $d_{50}$, and $d_{90}$ of the dispersed phase (particles and emulsion) in the sample fluid obtained using the flow-imaging method as compared with that obtained using standard laser diffraction from an analytical lab. As indicated, the $d_{50}$ and $d_{90}$ from these two methods are again in reasonable agreement. Moreover, the variation in $d_{10}$ is again likely attributed to the limitation on resolution of the present lens/filters in flow-imaging equipment, which again could be improved if required.

TABLE 2

| Dispersed Phase in Mud | LASER DIFFRACTION TECHNIQUE (ANALYTICAL LAB) (average of six runs) | FLOW IMAGING TECHNIQUE (Flow-CAM ES ™) (average of six runs) |
| --- | --- | --- |
| $d_{10}$ (µm) | 2.3 | 5.6 |
| $d_{50}$ (µm) | 16.6 | 18.5 |
| $d_{90}$ (µm) | 62.9 | 69.6 |

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A well system that includes a drill string extending from a surface location into a wellbore and defining an annulus between the drill string and the wellbore, a fluid circuit extending through the drill string to a bottom of the wellbore and back to the surface location within the annulus, and further extending back to the drill string from the annulus, and one or more flow imaging devices fluidly arranged in the fluid circuit to monitor the wellbore fluid and track a real-time particle size distribution (PSD) of one or more particulates suspended within the wellbore fluid.

B. A method that includes circulating a wellbore fluid through a fluid circuit of a well system including a drill string extending from a surface location into a wellbore, the fluid circuit extending through the drill string to a bottom of the wellbore and back to the surface location within an annulus defined between the drill string and the wellbore, and further extending back to the drill string from the annulus, monitoring the wellbore fluid with one or more flow imaging devices fluidly arranged in the fluid circuit, wherein the wellbore fluid is selected from the group consisting of drilling fluid, drill-in fluid, completion fluid, fracturing fluid, work-over fluid, a pill, a spacer, a sweep and any combination thereof, and determining a real-time particle size distribution (PSD) of one or more particulates suspended within the wellbore fluid with the one or more flow imaging devices.

C. A method that includes circulating a wellbore fluid through a fluid circuit of a well system including a drill string extending from a surface location into a wellbore, the fluid circuit extending through the drill string to a bottom of the wellbore and back to the surface location within an annulus defined between the drill string and the wellbore, and further extending back to the drill string from the annulus, obtaining an initial particle size distribution (PSD) of one or more particulates suspended within the wellbore fluid prior to introducing the wellbore fluid into the wellbore with a first flow imaging device fluidly arranged in the fluid circuit, obtaining a circulated PSD of the one or more particulates when the wellbore fluid exits the wellbore with a second flow imaging device fluidly arranged in the fluid circuit, receiving first and second output signals from the first and second flow imaging devices, respectively, with a signal processor, and generating with the signal processor a resulting output signal indicative of a difference between the initial and circulated PSD.

Each of embodiments A, B, and C may have one or more of the following additional elements in any combination: Element 1: wherein the wellbore fluid is selected from the group consisting of drilling fluid, drill-in fluid, completion fluid, fracturing fluid, work-over fluid, a pill, a spacer, a sweep, and any combination thereof. Element 2: wherein the one or more particulates are selected from the group consisting of weighting agents, lost circulation materials, wellbore cuttings, wellbore fines, neutral density particles, lightweight particles, particles added for stress cage applications, and any combination thereof. Element 3: wherein a first flow imaging device of the one or more flow imaging devices is fluidly arranged in the fluid circuit to monitor the wellbore fluid as it exits the wellbore. Element 4: wherein a second flow imaging device of the one or more flow imaging devices is fluidly arranged in the fluid circuit to monitor the wellbore fluid prior to being introduced into the wellbore. Element 5: further comprising a signal processor communicably coupled to the first and second flow imaging devices and configured to receive first and second output signals from the first and second flow imaging devices, respectively, and generate a resulting output signal indicative of a difference in the PSD of the one or more particulates changed based on the first and second output signals. Element 6: further comprising solids control equipment arranged in the fluid circuit to receive the wellbore fluid as it exits the wellbore, wherein a first flow imaging device of the one or more flow imaging devices is fluidly arranged in the fluid circuit prior to the solids control equipment and a second flow imaging device of the one or more flow imaging devices is fluidly arranged in the fluid circuit following the solids control equipment, and a signal processor communicably coupled to the first and second flow imaging devices and configured to receive first and second output signals from the first and second flow imaging devices, respectively, and generate a resulting output signal indicative of a difference in the PSD of the one or more particulates changed based on the first and second output signals. Element 7: wherein the one or more flow imaging devices comprise a flow chamber defining a capillary for conveying the wellbore fluid therethrough, a backlighting generator to provide light to the capillary, an image capturing system to capture images of the one or more particulates flowing through the capillary, and a computing device communicably coupled to the image capturing system and configured to receive captured images of the one or more particulates, wherein the computing device includes one or more library databases populated with image information relating to fluid components not of interest or to be accounted separately, the computing device being programmed to query the one or more library databases and omit the fluid components that are not of interest or to be accounted separately in determining the PSD of the one or more particulates. Element 8: wherein the one or more particulates comprise wellbore cuttings or fines and the PSD of the wellbore cuttings or fines in the wellbore fluid is indicative of cuttings disintegration in the wellbore.

Element 9: wherein determining the real-time PSD of the one or more particulates comprises at least one of determining the real-time PSD of the one or more particulates within the wellbore fluid as it exits the wellbore and determining the real-time PSD of the one or more particulates within the wellbore fluid as it enters the wellbore. Element 10: wherein the well system further comprises solids control equipment arranged in the fluid circuit to receive the wellbore fluid as it exits the wellbore, and wherein determining the real-time PSD of the one or more particulates comprises determining the real-time PSD of the one or more particulates within the wellbore fluid following the solids control equipment. Element 11: further comprising replenishing the wellbore fluid with at least one of lost circulation materials and weighting agents based on the real-time PSD of the one or more particulates within the wellbore fluid. Element 12: wherein determining the real-time PSD of the one or more particulates comprises determining a concentration of the one or more particulates in the fluid within the wellbore fluid. Element 13: wherein the one or more particulates are wellbore cuttings or fines, the method further comprising reducing a concentration of the wellbore cuttings or fines in the wellbore fluid based on the real-time PSD of the one or more particulates. Element 14: wherein reducing a concentration of the wellbore cuttings or fines in the wellbore fluid comprises at least one of diluting the wellbore fluid with a base oil, adding a shale stabilizer to the wellbore fluid, and processing the wellbore fluid within solids control equipment.

Element 15: wherein the one or more particulates are at least one of lost circulation materials (LCM) and weighting agents, the method further comprising replenishing the wellbore fluid with at least one of LCM and weighting agents when the difference between the initial and circulated PSD indicates a loss of the at least one of LCM and weighting agents. Element 16: wherein the one or more particulates are wellbore cuttings or fines, the method further comprising reducing a concentration of the wellbore cuttings or fines in the wellbore fluid when the difference between the initial and circulated PSD indicates an accumulation of the wellbore cuttings or fines. Element 17: wherein reducing the concentration of the wellbore cuttings or fines in the wellbore fluid comprises diluting the wellbore fluid with a base oil. Element 18: wherein reducing the concentration of the wellbore cuttings or fines in the wellbore fluid comprises adding a shale stabilizer to the wellbore fluid. Element 19: wherein reducing the concentration of the wellbore cuttings or fines in the wellbore fluid comprises processing the wellbore fluid within solids control equipment. Element 20: wherein the second flow imaging device comprises a computing device that includes one or more library databases populated with image information relating to fluid components not of interest, the method further comprising querying the one or more library databases with the computing device to omit the fluid components that are not of interest in determining the circulated PSD of the one or more particulates. Element 21: further comprising measuring at least one of a mud weight and a rheology of the wellbore fluid. Element 22: further comprising evaluating an equivalent circulating density of the wellbore fluid. Element 23: wherein the one or more particulates are wellbore cuttings or fines, the method further comprising determining whether there is sag in the wellbore based on the difference between the initial and circulated PSD.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:
1. A well system, comprising:
a drill string having an inlet and extending from a surface location into a wellbore and defining an annulus between the drill string and the wellbore;
a fluid circuit that circulates a wellbore fluid, the fluid circuit extending from the inlet, through the drill string to a bottom of the wellbore, back to the surface location within the annulus, and back to the inlet;
one or more flow imaging devices arranged in the fluid circuit to monitor the wellbore fluid and track a real-time particle size distribution of one or more particulates suspended within the wellbore fluid;

a first flow imaging device configured to monitor the wellbore fluid prior to being introduced to the wellbore and to generate a first output signal;

a second flow imaging device configured to monitor the wellbore fluid after exiting the wellbore and to generate a second output signal; and a signal processor communicably coupled to the first and second flow imaging devices to receive a first output signal from the first flow imaging device and a second output signal from the second flow imaging device, to generate a resulting output signal based on the first output signal and the second output signals, and indicative of a difference in the real-time particle size distribution of one or more particulates.

2. The well system of claim 1, wherein the wellbore fluid is selected from the group consisting of drilling fluid, drill-in fluid, completion fluid, fracturing fluid, work-over fluid, a pill, a spacer, a sweep, and any combination thereof.

3. The well system of claim 1, wherein the one or more particulates are selected from the group consisting of weighting agents, lost circulation materials, wellbore cuttings, wellbore fines, neutral density particles, lightweight particles, particles added for stress cage applications, and any combination thereof.

4. The well system of claim 1, further comprising:

solids control equipment arranged in the fluid circuit to receive the wellbore fluid exiting the wellbore, wherein a first flow imaging device of the one or more flow imaging devices is arranged in the fluid circuit prior to the solids control equipment and a second flow imaging device of the one or more flow imaging devices is arranged in the fluid circuit following the solids control equipment; and a signal processor communicably coupled to the first and second flow imaging devices to receive first and second output signals generated by the first and second flow imaging devices, respectively, and generate a resulting output signal, the resulting output signal being based on the first and second output signals and indicative of a difference in the real-time particle size distribution of one or more particulates changed.

5. The well system of claim 1, wherein the one or more flow imaging devices comprise:

a flow chamber defining a capillary for conveying the wellbore fluid therethrough;

a backlighting generator to provide light to the capillary;

an image capturing system to capture images of the one or more particulates flowing through the capillary; and a computing device communicably coupled to the image capturing system and configured to receive captured images of the one or more particulates, the computing device including one or more library databases populated with image information relating to fluid components not of interest or to be accounted separately, wherein the computing device is programmed to query the one or more library databases and omit the fluid components that are not of interest or to be accounted separately in determining the real-time particle size distribution of one or more particulates.

6. The well system of claim 1, wherein the one or more particulates comprise wellbore cuttings or fines and the real-time particle size distribution of one or more particulates of the wellbore cuttings or fines in the wellbore fluid is indicative of cuttings disintegration in the wellbore fluid.

7. A method, comprising:

circulating a wellbore fluid through a fluid circuit of a well system including a drill string having an inlet and extending from a surface location into a wellbore, the fluid circuit extending from the inlet through the drill string to a bottom of the wellbore and back to the surface location within an annulus defined between the drill string and the wellbore, the fluid circuit further extending back to the inlet from the annulus;

monitoring the wellbore fluid prior to introducing the wellbore fluid into the inlet and exiting the wellbore with one or more flow imaging devices arranged in the fluid circuit;

generating a first output signal with the one or more flow imaging devices prior to introducing the wellbore fluid into the inlet;

generating a second output signal with the one or more flow imaging devices from the wellbore fluid exiting the wellbore; and determining a real-time particle size distribution of one or more particulates suspended within the wellbore fluid with a resulting output signal from the first output signal and the second output signal, the resulting output signal indicative of a difference in the real-time particle size distribution of one or more particulates.

8. The method of claim 7, wherein determining the real-time particle size distribution of one or more particulates comprises at least one of determining the real-time particle size distribution of one or more particulates within the wellbore fluid exiting the wellbore and determining the real-time particle size distribution of one or more particulates within the wellbore fluid entering the inlet of the drill string.

9. The method of claim 7, wherein the well system further comprises solids control equipment arranged in the fluid circuit to receive the wellbore fluid exiting the wellbore, and wherein determining the real-time particle size distribution of one or more particulates comprises determining the real-time particle size distribution of one or more particulates within the wellbore fluid following the solids control equipment.

10. The method of claim 7, further comprising replenishing the wellbore fluid with at least one of lost circulation materials and weighting agents based on the real-time particle size distribution of one or more particulates suspended within the wellbore fluid.

11. The method of claim 7, wherein determining the real-time particle size distribution of one or more particulates comprises determining a concentration of the one or more particulates suspended within the wellbore fluid.

12. The method of claim 7, wherein the one or more particulates are wellbore cuttings or fines, the method further comprising reducing a concentration of the wellbore cuttings or fines in the wellbore fluid based on the real-time particle size distribution of one or more particulates.

13. The method of claim 12, wherein reducing a concentration of the wellbore cuttings or fines in the wellbore fluid comprises at least one of diluting the wellbore fluid with a base oil, adding a shale stabilizer to the wellbore fluid, and processing the wellbore fluid within solids control equipment.

14. A method, comprising:

circulating a wellbore fluid through a fluid circuit of a well system including a drill string having an inlet and extending from a surface location into a wellbore, the fluid circuit extending from the inlet through the drill string to a bottom of the wellbore and back to the surface location within an annulus defined between the drill string and the wellbore, the fluid circuit further extending back to the inlet from the annulus;

monitoring the wellbore fluid prior to introducing the wellbore fluid into the inlet with a first flow imaging device arranged in the fluid circuit;

generating a first output signal with the first flow imaging device, the first output signal being indicative of an initial particle size distribution of one or more particulates suspended within the wellbore fluid;

monitoring the wellbore fluid exiting the wellbore with a second flow imaging device arranged in the fluid circuit;

generating a second output signal with the second flow imaging device, the second output signal being indicative of a circulated particle size distribution of one or more particulates;

receiving the first and second output signals with a signal processor; and generating with the signal processor a resulting output signal indicative of a difference between the initial particle size distribution of one or more particulates and a circulated particle size distribution of one or more particulates.

15. The method of claim 14, wherein the one or more particulates are at least one of lost circulation materials (LCM) and weighting agents, the method further comprising replenishing the wellbore fluid with at least one of LCM and weighting agents when the difference between the initial particle size distribution of one or more particulates and a circulated particle size distribution of one or more particulates indicates a loss of the at least one of LCM and weighting agents.

16. The method of claim 14, wherein the one or more particulates are wellbore cuttings or fines, the method further comprising reducing a concentration of the wellbore cuttings or fines in the wellbore fluid when the difference between the initial particle size distribution of one or more particulates and a circulated particle size distribution of one or more particulates indicates an accumulation of the wellbore cuttings or fines.

17. The method of claim 16, wherein reducing the concentration of the wellbore cuttings or fines in the wellbore fluid comprises diluting the wellbore fluid with a base oil.

18. The method of claim 16, wherein reducing the concentration of the wellbore cuttings or fines in the wellbore fluid comprises adding a shale stabilizer to the wellbore fluid.

19. The method of claim 16, wherein reducing the concentration of the wellbore cuttings or fines in the wellbore fluid comprises processing the wellbore fluid within solids control equipment.

20. The method of claim 14, wherein the second flow imaging device comprises a computing device that includes one or more library databases populated with image information relating to fluid components not of interest or not to be accounted, the method further comprising querying the one or more library databases with the computing device to omit the fluid components that are not of interest or not to be accounted in determining the circulated PSD of the one or more particulates.

21. The method of claim 14, further comprising evaluating an equivalent circulating density of the wellbore fluid based on the first and second output signals.

22. The method of claim 14, wherein the one or more particulates are wellbore cuttings or fines, the method further comprising determining whether there is sag in the wellbore based on the difference between the initial particle size distribution of one or more particulates and a circulated particle size distribution of one or more particulates.

* * * * *